(12) United States Patent
Edwards et al.

(10) Patent No.: US 9,720,219 B2
(45) Date of Patent: Aug. 1, 2017

(54) LED ILLUMINATION

(71) Applicant: CoolLED Limited, Andover (GB)

(72) Inventors: Nicholas John Edwards, Devon (GB); Gerard Patrick Whoriskey, Hants (GB)

(73) Assignee: CoolLED Limited, Andover (GB)

( * ) Notice: Subject to any disclaimer, the term of this patent is extended or adjusted under 35 U.S.C. 154(b) by 0 days.

(21) Appl. No.: 14/761,228

(22) PCT Filed: Jan. 14, 2014

(86) PCT No.: PCT/GB2014/000007
§ 371 (c)(1),
(2) Date: Jul. 15, 2015

(87) PCT Pub. No.: WO2014/111674
PCT Pub. Date: Jul. 24, 2014

(65) Prior Publication Data
US 2015/0355448 A1    Dec. 10, 2015

(30) Foreign Application Priority Data
Jan. 15, 2013  (GB) .................... 1300660.6

(51) Int. Cl.
| G02B 21/06 | (2006.01) |
| G02B 27/30 | (2006.01) |
| G01N 21/64 | (2006.01) |
| G02B 27/14 | (2006.01) |
| G02B 21/16 | (2006.01) |

(52) U.S. Cl.
CPC ......... *G02B 21/06* (2013.01); *G01N 21/6458* (2013.01); *G02B 21/16* (2013.01); *G02B 27/141* (2013.01); *G02B 27/30* (2013.01); *G01N 2021/6463* (2013.01)

(58) Field of Classification Search
CPC ...... G02B 21/06; G02B 21/16; G02B 27/141; G02B 27/30; G01N 21/6458; G01N 2021/6463; G01N 2021/8636; G01N 2021/8645
USPC ............... 359/390; 362/249.02, 285, 311.02
See application file for complete search history.

(56) References Cited

U.S. PATENT DOCUMENTS

| 7,416,313 B2* | 8/2008 | Westphal ............... G02B 21/06 362/249.07 |
| 7,726,839 B2* | 6/2010 | Chien .................... F21S 8/035 362/249.03 |

(Continued)

FOREIGN PATENT DOCUMENTS

| EP | 1 918 757 A1 | 5/2008 |
| EP | 2 043 211 A  | 4/2009 |

(Continued)

*Primary Examiner* — Frank Font
(74) *Attorney, Agent, or Firm* — Muncy, Geissler, Olds & Lowe, P.C.

(57) ABSTRACT

The invention relates to an LED illumination device 1. Device 1 comprises at least two collimating optics 10,20,30,40 adapted to collimate light parallel to an illumination axis 2 through one or more dichroic mirrors 50,60,70, and at least two frames 12,22,32,42 each supporting at least two LED light sources, each frame being adapted to present one LED light source onto the focal axis 13,23,33,43 of one of said collimating optics.

7 Claims, 1 Drawing Sheet

(56) References Cited

U.S. PATENT DOCUMENTS

| | | | | |
|---|---|---|---|---|
| 7,852,553 | B2* | 12/2010 | Tsutsui | G02B 6/4206 359/385 |
| 7,898,665 | B2* | 3/2011 | Brukilacchio | A61B 1/0653 356/417 |
| 8,152,336 | B2* | 4/2012 | Alexander | F21V 15/01 362/147 |
| 8,242,462 | B2* | 8/2012 | Jaffe | G01J 1/58 250/458.1 |
| 8,275,226 | B2* | 9/2012 | Berman | G02B 21/0032 359/368 |
| 8,596,815 | B2* | 12/2013 | Lee | G02B 21/16 359/385 |
| 9,217,561 | B2* | 12/2015 | Jaffe | F21V 29/004 |
| 9,235,039 | B2* | 1/2016 | Lee | G02B 21/06 |
| 9,629,554 | B2* | 4/2017 | Ghosh | G02B 21/16 |
| 2004/0156098 | A1* | 8/2004 | Dubois | G01N 21/6458 359/368 |
| 2005/0128441 | A1* | 6/2005 | Morgan | G03B 21/2033 353/102 |
| 2005/0195388 | A1* | 9/2005 | Huang | G01M 11/00 356/237.1 |
| 2005/0224692 | A1* | 10/2005 | Tsuchiya | G01N 21/6458 250/201.3 |
| 2006/0215009 | A1* | 9/2006 | Amarakoon | G03G 15/0152 347/118 |
| 2006/0227302 | A1 | 10/2006 | Harbers et al. | |
| 2007/0053058 | A1 | 3/2007 | Angelini et al. | |
| 2009/0121154 | A1 | 5/2009 | Westphal et al. | |
| 2009/0201577 | A1* | 8/2009 | Laplante | G01N 21/6458 359/355 |
| 2009/0268460 | A1* | 10/2009 | Van Gorkom | H01L 25/0753 362/244 |
| 2010/0201804 | A1* | 8/2010 | Pellegrino | G01N 21/8806 348/92 |
| 2010/0321772 | A1* | 12/2010 | Reimer | A61B 1/043 359/385 |
| 2011/0122402 | A1 | 5/2011 | Westphal | |
| 2012/0062723 | A1* | 3/2012 | Ghosh | G02B 21/16 348/79 |
| 2012/0147332 | A1 | 6/2012 | Huang | |
| 2012/0242912 | A1 | 9/2012 | Kitano | |
| 2012/0287244 | A1* | 11/2012 | Bennett | G01N 21/6458 348/46 |
| 2012/0307514 | A1 | 12/2012 | Brukilacchio et al. | |
| 2014/0233095 | A1* | 8/2014 | Lee | G02B 21/06 359/385 |

FOREIGN PATENT DOCUMENTS

| | | |
|---|---|---|
| JP | 2002-350732 A | 12/2002 |
| JP | 2005-10296 A | 1/2005 |
| WO | WO 2004/070366 A1 | 8/2004 |
| WO | WO 2009/001390 A1 | 12/2008 |

* cited by examiner

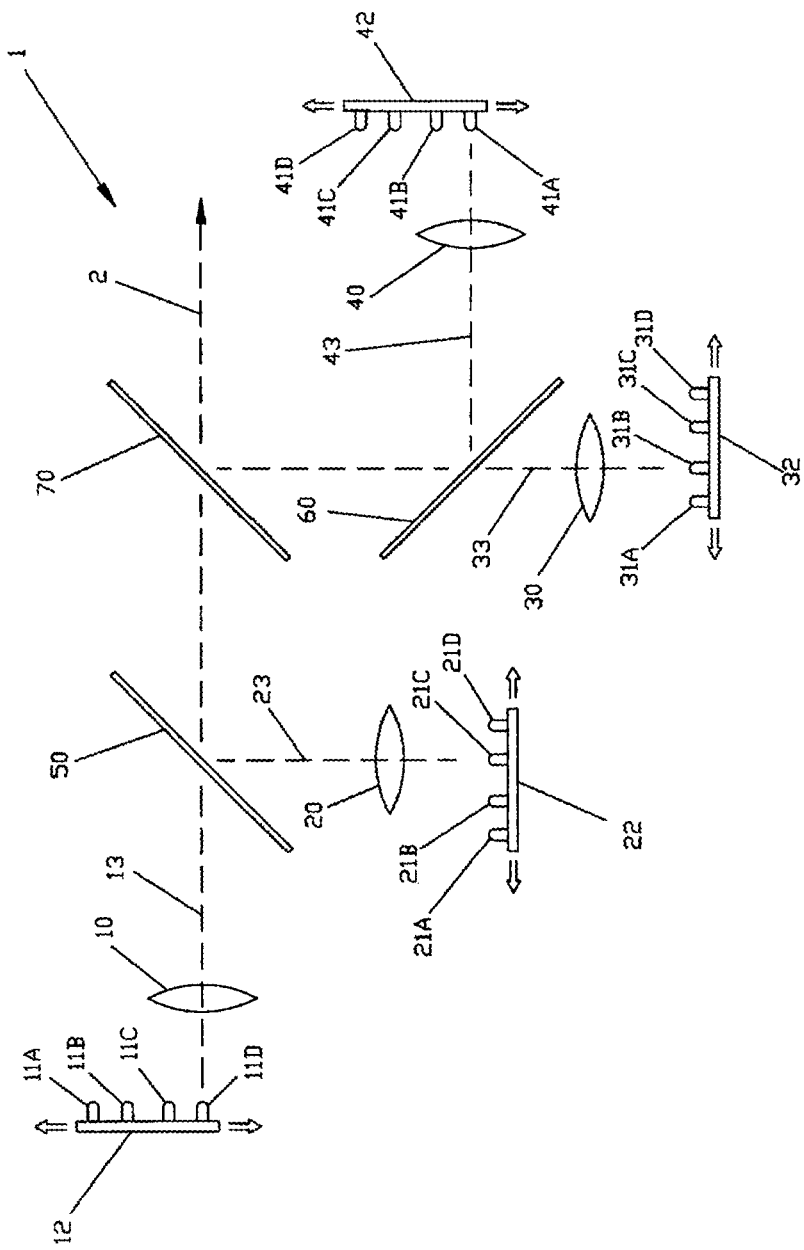

LED ILLUMINATION

The present invention relates to LED, phosphor and other solid state illumination, especially for fluorescence microscopy.

It is known to tag biological cells with a fluorescent dye (or fluorochrome), which are then illuminated with LED lights of a specific colour or wavelength band. When these dyes are excited with light of a specific colour they undergo a process known as Stokes Shift resulting in light of a longer wavelength being emitted. Viewing these emissions provides important information to the biologist as to the composition and state of cells under investigation with a microscope.

Often it is required to illuminate cells with up to four different wavelengths either at the same time, or rapid switching between any of the four. It may also be desirable to select the four wavelengths from as wide a range as possible across the spectrum from near UV to IR. A selection from a quantity of 12 to 16 wavelengths would cover more than 95% of the applications.

Because the light being transmitted has to be highly collimated by using collimating optics, it is not possible to collimate light from several sources through the same optics since each light source cannot lie on the focal axis of the optics.

It is known practice to have say three or four LED light sources and direct light from each source through individual collimating optics as parallel light onto a common axis using dichroic mirrors. This allows light from more than one LED to be collimated on to a single axis. This means however that light from some of the LEDs will need to pass through one or several dichroic mirrors. However dichroic mirrors are typically only 95% or so efficient, so unacceptable light losses occur if the light needs to pass through more than say two mirrors. This limits the number of LED sources which can be used. In addition, for every LED source, there is a requirement for collimating optics, drive electronics, and thermal management and a dichroic mirror for every additional wavelength above the first. So while it might be technically possible to create a light source from multiple wavelengths in excess of 4, the incremental costs result in a non competitive solution.

The invention seeks to provide a solution to this problem.

According to the present invention there is provided an LED illumination device comprising:

a) at least two collimating optics adapted to collimate light parallel to an illumination axis through one or more dichroic mirrors, and b) at least two frames each supporting at least two LED light sources, each frame being adapted to present one LED light source onto the focal axis of one of said collimating optics.

Preferably one collimating optics are on the illumination axis, and the or each other collimating optics collimates light parallel to an illumination axis through one or more dichroic mirrors.

Preferably there are four collimating optics and four frames. Preferably each frame supports four LED light sources. Preferably there are three dichroic mirrors.

Preferably the plates move relative to the focal axis of one of said collimating optics, to present one LED light source to the focal axis.

An embodiment of the invention will now be described with reference to the accompanying drawing showing a schematic diagram of an LED illumination device.

Referring to the drawing there is shown an LED illumination device 1 to deliver light to an epi-fluorescence port of a fluorescence microscope on an illumination axis 2.

Four collimating optics 10, 20,30,40 are provided to collimate light parallel from LEDs to the illumination axis through three dichroic mirrors 50,60,70.

Collimating optics 10 receives light at any one time from one of four LED light sources 11A,11B,11C,11D on a frame 12. Frame 12 can move left and right relative to the collimating optics axis 13 so that any one of the light sources is on the collimating optics axis 13. Light from collimating optics 10 is focused into parallel light which passes through dichroic mirror 50, through dichroic mirror 70 and emerges onto the illumination axis 2.

Collimating optics 20 receives light at any one time from one of four LED light sources 21A,21B,21C,21D on a frame 22. Frame 22 can move left and right relative to the collimating optics axis 23 so that any one of the light sources is on the collimating optics axis 23. Light from collimating optics 20 is focused into parallel light which is reflected by dichroic mirror 50, passes through dichroic mirror 70 and emerges onto the illumination axis 2.

Collimating optics 30 receives light at any one time from one of four LED light sources 31A,31B,31C,31D on a frame 32. Frame 32 can move left and right relative to the collimating optics axis 33 so that any one of the light sources is on the collimating optics axis 33. Light from collimating optics 30 is focused into parallel light which passes through dichroic mirror 60, is reflected by dichroic mirror 70 and emerges onto the illumination axis 2.

Collimating optics 40 receives light at any one time from one of four LED light sources 41A,41B,41C,41D on a frame 42. Frame 42 can move left and right relative to the collimating optics axis 43 so that any one of the light sources is on the lens axis 43. Light from lens 40 is focused into parallel light which is reflected by dichroic mirror 50, and is reflected by dichroic mirror 70 and emerges onto the illumination axis 2.

It is envisaged that the light sources 41A,41B,41C,41D may cover the spectral range of 365 nm-440 nm. The light sources 31A,31B,31C,31D may cover the spectral range of 440 nm-510 nm. The light sources 21A,21B,21C,21D may cover the spectral range of 510 nm-590 nm. The light sources 11A,11B,11C,11D may cover the spectral range of 590 nm-850 nm.

It will be appreciated that at any one time up to four different light sources of different wavelength and of spectrally separate peaks can be directed onto the illumination axis 2. It will also be seen that no light source need pass through more than two mirrors and this results in low light level losses, even though light from sixteen different light sources can be selected. The invention allows convenient switching between light sources using simple mechanical movement of the plates supporting the LED.

It is envisaged that each light source would be a single high power LED or LED array of suitable wavelength peak to excite fluorochromes. Suitable drive circuits and thermal management systems for the LEDs would be required as is known in the art.

The invention may take a form different to that specifically described above. For example two or three or more than four LED light sources could be provided for each collimating optics. Also more than four collimating optics or two or three collimating optics could be provided. While the mechanical movement of the LED frames has been described in a linear direction, a rotational movement could also be considered.

Further modifications will be apparent to those skilled in the art without departing from the scope of the present invention.

The invention claimed is:

1. An LED illumination device comprising:
a) at least four collimating optics, each of the at least four collimating optics adapted to collimate light parallel to an illumination axis through one or more dichroic mirrors, and
b) at least four frames, including a first frame, a second frame, a third frame, and a fourth frame, each frame supporting at least two LED light sources, each frame being moveable to present the LED light sources onto a focal axis of the at least four collimating optics,
wherein the at least two LED light sources are supported by the first frame emit only within a spectral range of 365 nm to 440 nm,
wherein the at lest two LED light sources are supported by the second frame emit only within a spectral range of 440 nm to 510 nm,
wherein the at least two LED light sources are supported by the third frame emit only within a spectral range of 510 nm to 590 nm, and
wherein the at least two LED light sources are supported by the fourth frame emit only within a spectral range of 590 nm to 850 nm.

2. The LED illumination device according to claim 1, wherein one of the at least four collimating optics is on the illumination axis, and another of the at least four collimating optics collimates light parallel to the illumination axis through the one or more dichroic mirror.

3. The LED illumination device according to claim for 2, wherein there are the first collimating optic, the second collimating optic, a third collimating optic, and a fourth collimating optic.

4. The LED illumination device according to claim 1 or 2, wherein each of the at least four frames supports four LED light sources.

5. The LED illumination device according to claim 1 or 2, wherein there are three dichroic mirrors.

6. The LED illumination device according to claim 1 or 2, wherein each of the at least four frames move relative to the focal axis of one of said collimating optics, to present one LED light source to the focal axis.

7. A microscope incorporating a LED illumination device according to claim 1.

* * * * *